US005491552A

United States Patent [19]
Knüttel

[11] Patent Number: 5,491,552
[45] Date of Patent: Feb. 13, 1996

[54] OPTICAL INTERFEROMETER EMPLOYING MUTUALLY COHERENT LIGHT SOURCE AND AN ARRAY DETECTOR FOR IMAGING IN STRONGLY SCATTERED MEDIA

[75] Inventor: Alexander Knüttel, Rockville, Md.

[73] Assignee: Bruker Medizintechnik, Rheinstetten, Germany

[21] Appl. No.: 219,504

[22] Filed: Mar. 29, 1994

[30] Foreign Application Priority Data

Mar. 29, 1993 [DE] Germany ........................... 43 10 209.3

[51] Int. Cl.[6] ..................................................... G01B 9/02
[52] U.S. Cl. ............................................. 356/360; 356/351
[58] Field of Search ................................... 356/349, 351, 356/359, 360

[56] References Cited

U.S. PATENT DOCUMENTS

| | | | |
|---|---|---|---|
| 4,832,489 | 5/1989 | Wyant et al. | 356/359 |
| 4,978,219 | 12/1990 | Bessho | 356/359 |

OTHER PUBLICATIONS

"Stationary Depth Profiling Reflectometer, etc.", Kuttel et al., Optics Communications, vol. 102, No. 3, pp. 193–198; 1993.
"Imaging Through Random Scattering Media, etc.", Chiang et al., Optics Letters, vol. 18, No. 7, pp. 546–548; 1993.
"Fourier Transform Spectrometer, etc.", Okamoto et al, Applied Optics, vol. 23, No. 2, pp. 269–273; Jan. 1984.
"Partially Multiplexing Sensor, etc.", Liu et al., Applied Optics, vol. 32, No. 7, pp. 1100–1103; Mar. 1993.
"Experimental Verification of Image Detection, etc.", Toida et al., Electronics Letters, vol. 26, No. 11, pp. 700–702; May 1990.
"High Resolution Reflectometry in Biological Tissues", Clivaz et al., in Optics Letters, vol. 17, No. 1, pp. 4–6., Jan. 1992.
"Optical Coherence Domain Reflectometry, etc.", Youngquist et al., in Optical Letters, vol. 12, No. 3, pp. 158–160; Mar. 1987.
"Diode Laser Direct Modulation Heterodyne Interferometer", Tatsuno et al., in Applied Optics, vol. 26, No. 1, pp. 37–40. Jan. 1987.
New measurement system for fault location in optical wave–guide devices based on an interferometric technique Kazumasa Takada et al., Applied Optics, vol. 26, No. 9 May 1987, pp. 1603–1606.
Rayleigh backscattering measurement of single–mode fibres by low coherence optical time–domain reflectometer with 14 m spatial resolution, Appl. Phys. Lett. 59 (2) Jul. 1991 by Kazumasa Takada et e. pp. 143ff.

(List continued on next page.)

*Primary Examiner*—Samuel A. Turner
*Assistant Examiner*—Robert Kim
*Attorney, Agent, or Firm*—Bookstein & Kudirka

[57] ABSTRACT

In an optical imaging apparatus for the investigation of strongly scattering media, in particular biological tissue samples, with at least one-dimensional position resolution in a depth direction of a measuring object, with a radiation source for radiating low coherence light, with a device for splitting the low coherence light into two partial beams, of which one is guided in an object arm to the measured object and the other in a reference arm to a reflecting element, and with a detector configuration to which the partial beams reflected from the reflecting element in the reference arm and from the measured object in the object arm can be guided, brought into interference with another, and detected, the detector configuration exhibits a spatial extent transverse to the incident direction of both partial beams on the detector configuration along which light signals can be recorded in a position sensitive and simultaneous fashion and both partial beams in the object arm and in the reference arm are so guided that a spatial interference pattern occurs along the lateral extent of the detector configuration, whereby the reflecting element in the reference arm exhibits only static parts which, in any event, are non-mechanically moving. In this fashion a simple and economical as well as especially mechanically stable reflectometer apparatus is achieved with which a rapid sequence of image recordings is possible.

24 Claims, 5 Drawing Sheets

OTHER PUBLICATIONS

High–resolution reflectometry in biological tissues by X. Clivaz et al. Optics Letters vol. 17, No. 1, 1992, p. 4ff.

High–speed optical coherence domain reflectometry, by E. A. Swanson et al. Optics Letters vol. 17, No. 2, 1992, p. 151ff.

Fourier–Transform Spectroscopy Using Holographic Imaging Without Computing And With Stationary Interferometers, by G. W. Stroke and A. T. Funkhouser, Physics Letters, vol. 16, No. 3 (1965), pp. 272ff.

Fourier transform spectrometer with a self–scanning photo–diode array, by Takayuki Okamoto et al., Applied Optics, vol. 23, No. 2 (1984), p. 269ff.

Spatially Encoded Fourier Transform Spectroscopy in the Ultraviolet to Near–Infrared by J. V. Sweedler and M. Bonner Denton. Applied Spectroscopy, vol. 43, No. 8, (1989) pp. 1378ff.

Performance limits of stationary Fourier spectrometers by M. L. Junttila et al., Optical Society of America, vol. 8, No. 9 (1991), pp. 1457 ff.

OPTICAL INTERFEROMETER EMPLOYING MUTUALLY COHERENT LIGHT SOURCE AND AN ARRAY DETECTOR FOR IMAGING IN STRONGLY SCATTERED MEDIA

BACKGROUND OF THE INVENTION

The invention concerns an optical imaging apparatus for the investigation of strongly scattering media, in particular biological tissue samples with at least one-dimensional position resolution which always includes the depth direction of a measured object, with a radiation source for the emission of light with short coherence lengths of less than 0.1 mm, with a device for splitting the low coherence light into two partial beams from which one is introduced into an object arm to the measured object and the other into a reference arm to a reflecting element and including a detector configuration onto which the partial beams from the reflecting element in the reference arm and from the measured object in the object arm can be guided, caused to come into interference with another, and detected.

An apparatus of this kind is, for example, known from the publication of Clivaz et al., OPTICS LETTERS Vol. 17, no. 1 (1992) 4–6. Similar devices are also disclosed in Takata et al., APPLIED OPTICS, Vol. 26, no. 9 (1987) 1603–1606, Takata et al., APPLIED PHYSICS LETTERS 59 (2) (1991) 143–145 or Swanson et al., OPTICS LETTERS Vol. 17, no. 2 (1992) 151–153.

Optical imaging in strongly scattering materials, for example in vivo tissue, is being increasingly used as an auxiliary means in medical research and diagnostics. "Classical" optical methods as, for example, microscopy cannot be utilized in strongly scattering materials since the mean free wave length, along which the light beam remains undeflected, assumes values less than 100 µm. This means, that utilizing geometrical optics (e.g. confocal microscopy) it is not possible to achieve a penetration depth larger than 50 to 100 µm since the diffuse scattered light portion increases exponentially and ruins the contrast of the images.

The most important methods for three-dimensional imaging up to depths of several millimeters in strongly scattering materials is based, on the one hand, on low coherence and, on the other hand, on short-time-interferometry. Both methods distinguish themselves essentially only through their light sources, whereby the emitted radiation in both cases exhibits short coherence lengths of typically 10 to 30 µm. With low coherence interferometry an inexpensive incoherent light source (for example SLD or LED) is utilized, whereas for short-time interferometry an expensive (coherent) mode-locked laser which produces short light pulses is utilized.

The frequently utilized Michelson-interferometer is described briefly below. The collimated light of the light source is split by means of a beam-splitter and is incident in the reference arm on a mirror and in the object arm, after appropriate focusing, on the object. After reflection from a point of the object and from the mirror the light is joined together once more in the beam-splitter and, subsequently, is detected by, for example, a photodiode. When the optical path length of the object arm (defined by the mid-point of the beam-splitter and a point in the object) and that of the reference arm are identical up to a deviation on the order of the coherence length, both signals interfere at the detector. In order to easily detect an AC-signal (in contrast to a DC) the reference mirror is normally caused to oscillate at an appropriate frequency, along the optical axis with small deflections. During a mechanical displacement of the reference mirror along the optical axis, the depth of the object is sampled point for point. The strong scattering properties of the object do not influence the quality of the (one-dimensional) image since only the unscattered coherent components contribute to the AC-signal. However, due to the exponential fall-off of the coherent component of the signal only limited penetration depths are possible (see for example M. R. Hee et al., J. OPT. SOC. AM. B, Vol. 9, No. 6 (1992) 903–908).

The known devices are complicated and expensive due to the mechanically displaced reference mirror, are mechanically sensitive, and relatively slow since each point along the depth direction must be recorded in time sequence.

It is therefore the object of the present invention to introduce an optical apparatus of the above mentioned kind which is simple and cost effective, while being stable and insensitive with respect to mechanical interference, and which facilitates the taking of images in relatively rapid sequence.

SUMMARY OF THE INVENTION

This object is achieved in accordance with the invention in that the detector configuration exhibits a spatial extent transverse to the direction of incidence of both partial beams on the detector configuration over which the light signals can be recorded in a position sensitive and simultaneous fashion, and in that both partial beams are guided in the object arm and in the reference arm in such a fashion that a spatial interference pattern forms along the lateral extent of the detector configuration due to laterally spaced virtual light sources, whereby the reflecting element in the reference arm is static but exhibits portions which vibrate in the micron range.

The invention takes advantage of the principle of low coherence (or short-time) interferometry, however the applied one- or multidimensional (1D–3D) imaging procedure is stationary, e.g. no mechanically moving parts are needed and the imaging information is recorded in parallel by the detector and not in time sequence.

Stationary Fourier-transform spectrometers without imaging properties are, known for example, from Juntila et al., J. Opt. Soc. Am. A, Vol. 8, No. 9 (1991) 1457–1462, Stroke et al., Phys. Lett. Vol. 16, No. 3 (1965) 272–274 or Okamoto et al., Appl. Opt., Vol. 23, No. 2 (1984) 269–273.

In these known spectrometers a temporal interferogram is replaced by a spatial interferogram, from which, by means of Fourier transformation, a spectrum is produced. The known spectrometers are not suited for imaging, in particular in the event of strongly scattering media and, in particular, do not permit of a spatial resolution in the depth direction of the measured object.

In the inventive apparatus object signals along a line in the depth direction can be simultaneously transformed into a lateral dimension and detected with an appropriately configured detector. Due to the stationary construction an increased stability with respect to the mechanical shaking takes place and the device is, in general, constructed in a simple fashion and therefore is inexpensive to produce while allowing for very fast recording sequences.

In a particularly simple embodiment of the inventive optical apparatus, the object arm and the reference arm are parts of a Michelson interferometer. Other constructive forms of the interferometer portion of the inventive device are, however, also conceivable, for example, interferometers as described and shown in Junttila et al. *J. Opt. Soc. Am. A*, Vol. 8, No. 9 (1991) 1457–1462.

In an embodiment of the invention two-dimensional images can be detected by the detector configuration. In this fashion the imaging comprises, in addition to the depth dimension, a further lateral spatial dimension.

Towards this end, in an improvement of this embodiment, the radiation source includes an array of point-light sources which is arranged laterally to the radiation direction, in particular, a linear array. In this fashion a plurality of point sources can be arranged next to each other and simultaneously emit light.

In another embodiment a device for non-mechanical lateral deflection of the light emitted by the radiation source is provided for, along the direction of the radiated light, following the radiation source. In this fashion a lateral distribution of the light emanating from the radiation source can also be achieved. Likewise as in the previously mentioned embodiment in addition to the depth dimension, a lateral dimension of the object to be investigated can, in this fashion, also be sampled.

In a further embodiment of the optical apparatus in accordance with the invention, devices for three-dimensional imaging are provided for.

These can, in one example of an embodiment, include a device arranged along the direction of the radiated light downstream of the radiation source for non-mechanical deflection in a lateral direction, for example x, of the light emitted from the radiation source, whereby the radiation source itself includes an array of point light sources arranged in, for example, the y-direction laterally to the radiation direction, in particular, a linear array.

A further possibility for the realisation of three-dimensional images is given in that a second device for the non-mechanical lateral deflection is provided for which deflects the light emitted from the radiation source into a direction transverse to the deflection direction of the first of device for non-mechanical lateral deflection.

In a particularly preferred embodiment, a device for frequency modulation of the optical frequency of the light of both partial beams is provided for. In this fashion AC-signals can be produced in the detector configuration, whereby the utilization of a lock-in-measuring procedure is rendered possible which serves to suppress the noise background.

The modulation of the phase difference can be effected by an embodiment in which the reflecting element in the reference arm is a reflector vibrating with a defined frequency, in particular, is a vibrating mirror with amplitudes in the μm range. A mirror of this kind can displace the optical frequency of the reflected light in the frequency range from approximately 1 to 100 kHz. The optical detectors which are normally used display no problems in detecting the amplitude modulated signals of this frequency from the interference.

In another embodiment a non-mechanical deflecting unit is provided for in the optical path of the partial beam in the reference arm, with which the corresponding partial beam can be given a particular frequency displacement. A non-mechanical deflecting unit of this type is mechanically more robust and, in general, is more compact than a vibrating mirror.

In an improvement of this embodiment, the device for frequency modulation can include a piezoelectric element. In another improvement, the deflection device can be an acoustical optical modulator. With deflecting devices of this kind the deflected beam receives a superimposed frequency of approximately 80 MHz.

This relatively high frequency can no longer be resolved by some of the known detector configurations such as, for example, CCD-cameras. Towards this end, in a preferred improvement of the above mentioned embodiment, a microchannelplate (MCP) with a device for gate driven amplitude modulation is provided for, as viewed in the direction of the incident light, before the detector configuration. The high frequency modulated light incident on the MCP can, by switching between the amplifier and the rejection modes, be transformed from the initial circa 80 MHz, into the range of several kHz and below so that the detection can take place using a classical detector unit (CCD-camera) in a frequency resolved fashion.

In another embodiment a further non-mechanical deflection device is provided for, as viewed in the direction of the incident light, before the detector configuration which displaces back the frequency of the incident light which had already been displaced by approximately 80 MHz by a slightly different high frequency, so that it finally reaches the detector with a long wave length beat frequency in the Kilohertz region, which corresponds to the difference frequency.

In an alternative embodiment the radiation source exhibits a device for amplitude modulation of the emitted light with a slightly different high frequency with respect to the non-mechanical deflection device. Also in this fashion the high frequency superimposed by the non-mechanical deflection device onto the light beam, for example 80 MHz, can be reduced to a magnitude which can be time resolved by the known detector devices.

In a particularly simple embodiment of the optical apparatus in accordance with the invention the detector configuration includes a laterally extending photodiode array. The array can be either linearly or areally arranged.

In an alternative embodiment the detector configuration includes a CCD-camera (charge-coupled device) as for example is known per se from Sweedler et al., APPLIED SPECTROSCOPY, Vol. 43, No. 8 (1989) 1378–1384.

The radiation sources, in embodiments of the invention, can include a light emitting diode (LED) and, in other embodiments, a super-luminescent diode (SLD) or another source with a short coherence length such as a short-time or pulsed laser.

Instead of point sources, a laterally extended, in particular, an areally emitting lamp can be utilized which renders such an embodiment particularly economical. Since, in any event, only light with short coherence lengths of less than 0.1 mm can be used, it is possible to do without an expensive laser device or laser diode.

In a particularly preferred embodiment the inventive optical apparatus is a free space device. In other embodiments fiber optic elements can also be used.

The use of the above described optical apparatus for optical spectroscopy or spectrometry also falls within the framework of the present invention. The peak values recorded in the interferogram of the detected AC-modulated light exhibit, namely, a fine structure, e.g. the peaks are envelopes with a carrier frequency. The carrier frequency can, however, also be superimposed with spectroscopic information concerning the spectral distribution in addition to the spatial information which is supplied by the peaks of the interferogram.

The invention is more closely described and explained below with the embodiments represented in relation to the drawing. The features which can be derived from the description and the drawing can also find application in other embodiments of the invention either individually or collectively in arbitrary combination.

DESCRIPTION OF THE PREFERRED EMBODIMENT

Low coherence interferometry has become an important tool for a contactless depth profiling of optical fibres, integrated optics, and biological structures in the reflection mode with high spatial resolution. In all of the current reflectance interferometers a depth sampling is achieved by means of a moving mirror. Although there are apparatuses with high mirror movement speeds, in many applications, it is necessary to take data at speeds which are too fast for mechanically moving parts. In biological and medical diagnostics, measurements must be carried out at times which are fast with respect to the motion of a patient. For the control of process and assembly lines, a rapid recording of data is necessary for high through-put. In addition dedicated apparatuses can be rendered compact and robust at low cost.

The apparatus in accordance with the present invention is the first depth profiling reflectometer based on the principle of interference measurements with low coherence with which no mechanically moving parts are utilized.

Figure 1:
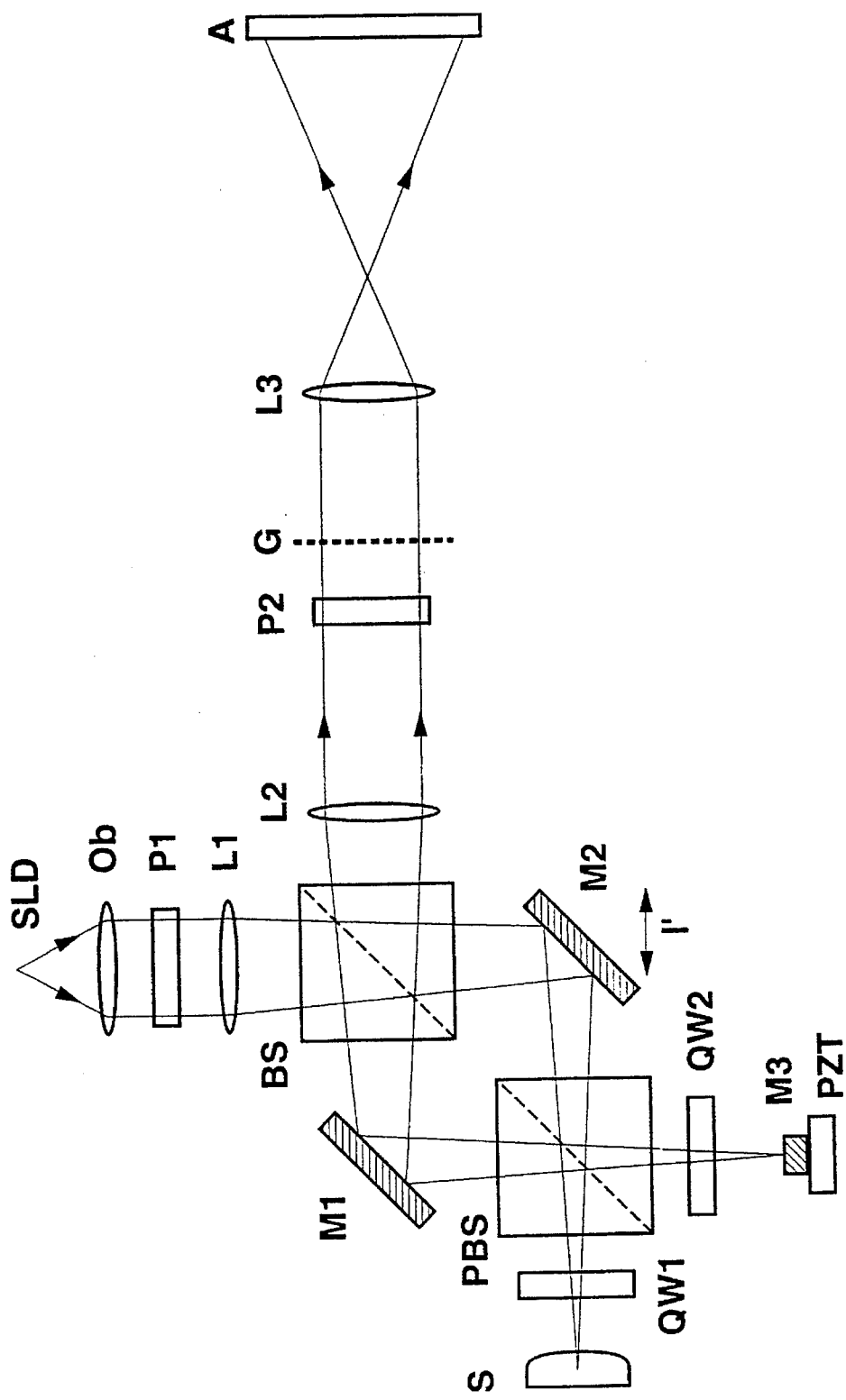
FIG. 1 shows a functional diagram of a stationary optical reflectometer according to the invention.

The optical construction of an inventive stationary reflectometer is shown in FIG. 1. The essential portion of the reflectometer is a Michelson interferometer, which is part of a Sagnac type interferometer with perpendicular light paths. In the Michelson-interferometer, the light from the source is split into two beams by a polarizing beam-splitting cube PBS. The partial beams are directed to an object arm and a reference arm which terminate at the sample S and the reference mirror M3, which is connected to a piezoelectric converter PZT, respectively. The Sagnac type interferometer consists of a non-polarizing beam-splitting cube BS and two mirrors M1 and M2.

Light coming from a wide band super-luminescent diode SLD having a very small emission surface, is collimated by means of objective lens Ob (×10) in a parallel fashion to a beam diameter of 7 mm. The lens L1, having a focal length of f=150 mm, focuses light onto the sample and onto the mirror M3. After back-reflection the object and reference beams are back-collimated once more by the lens L2 (F=150 mm). Interference fringes with varying separations appear as a function of the position 1' of M2 relative to M1 and are directed horizontally (in the plane of FIG. 1) in the grid plane located at the rear focal point of L2. The grid G (80 L/mm) overlaps the spatial frequency of the interference pattern up to a small spatial frequency, in order to facilitate a detection by means of a linear photodiode configuration with low resolution. The imaging lens L3 (f=62,5 mm) shown in FIG. 1 (optional) enlarges the Moire pattern, whereby the capability of the large-element detector configuration to resolve small optical paths differences is further improved.

In order to guarantee an optimized through-put, the polarization state of the light must be precisely adjusted at various locations in the interferometer. The polarizer P1 only allows vertically polarized light (the polarization plane is perpendicular to the plane of FIG. 1) to penetrate into the interferometer. After the light has been split by the non-polarizing beam-splitting cube BS, the two exiting partial beams are only reflected within the polarizing beam-splitter PBS onto the sample or the mirror M3 and are not transmitted. In order, in the Sagnac type interferometer, to establish an optical path in the clockwise and counter clockwise directions, it is necessary for the light reflected from the sample S and from the mirror M3 to penetrate through the polarizing beam-splitting cube. In order to achieve this, the polarization direction of the light is rotated horizontally (plane of FIG. 1) in that the light is guided twice through each of the quarter wave plates QW1 and QW2. The polarization direction of the polarizer P2 is adjusted to the horizontal direction in order to prevent residual vertically polarized light from reaching the detector configuration A. If all optical elements were perfect and if the mirrors M3 and the sample S would perfectly reflect the circularly polarized light (which is unlikely, in particular in the event of a non-mirror-reflecting sample) then the signal efficiency of the present interferometer would be the same as that of the non-modified Sagnac interferometer.

In order to reduce the noise background, the optical interference pattern is phase modulated in that a mirror M3 is vibrated with 30 kHz by means of a piezoelectric converter PZT. Since the displacement of the PZT has the value which is only a fraction of a wave length, the current method can be clearly considered to be a stationary one. Spatially heterodyne superimposed mixtures (in order to facilitate the use of detector configurations with low resolution) as well as temporarily homodyne mixtures (in order to improve the signal to noise) are utilized in the reflectometer.

Figure 2A:
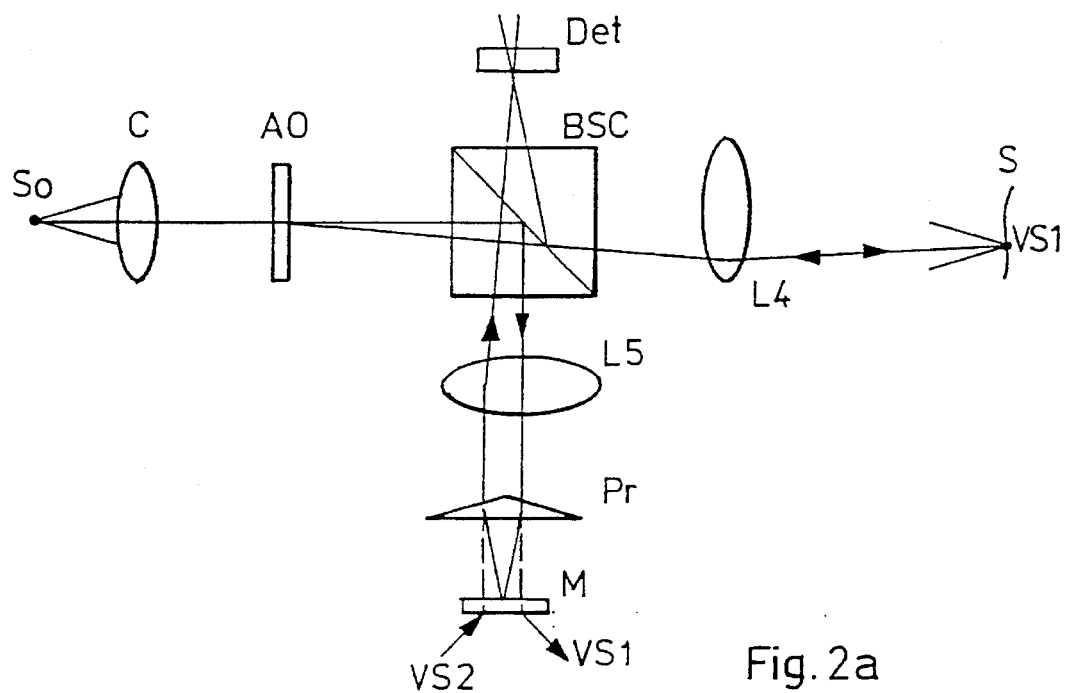
FIG. 2a shows a schematic functional diagram of an inventive reflection configuration for 2D-imaging.

FIG. 2a shows a particularly preferred embodiment of a reflection device (relative to the object) for 2D-imaging. Light emitted from an incoherent point shaped light source So is collimated with the assistance of a lens C into a parallel light beam of approximately 10 mm diameter. Approximately 50% of the light is non-mechanically deflected (for example by means of an acoustic optical modulator AO) whereas the other 50% passes the component without being influenced. The beam deflected by AO directly passes a beam-splitter BSC and is focused onto an object S by means of a lens L4. The point source thereby produced corresponds to a virtual source VS1 as explained in more detail in FIG. 4 and below.

The beam which is not deflected by AO is bent away at right angles by means of the beam-splitter BSC and focused by means of lens L5 onto a mirror M. A prism Pr (or a combination of mirrors) displaces the virtual source VS2 along the mirror in the lateral direction. The point of intersection of the dashed line with the mirror shows the displacement of VS2 relative to VS1 as described more closely below. The object and reference beams which are recollimated after reflection meet after the beam-splitter BSC at a detector Der (for example a 1D-CCD-camera or photodiode-array) to interfere. The depth information of the object is transferred onto the detector for every point in the lateral direction in a single "shot".

Figure 2B:
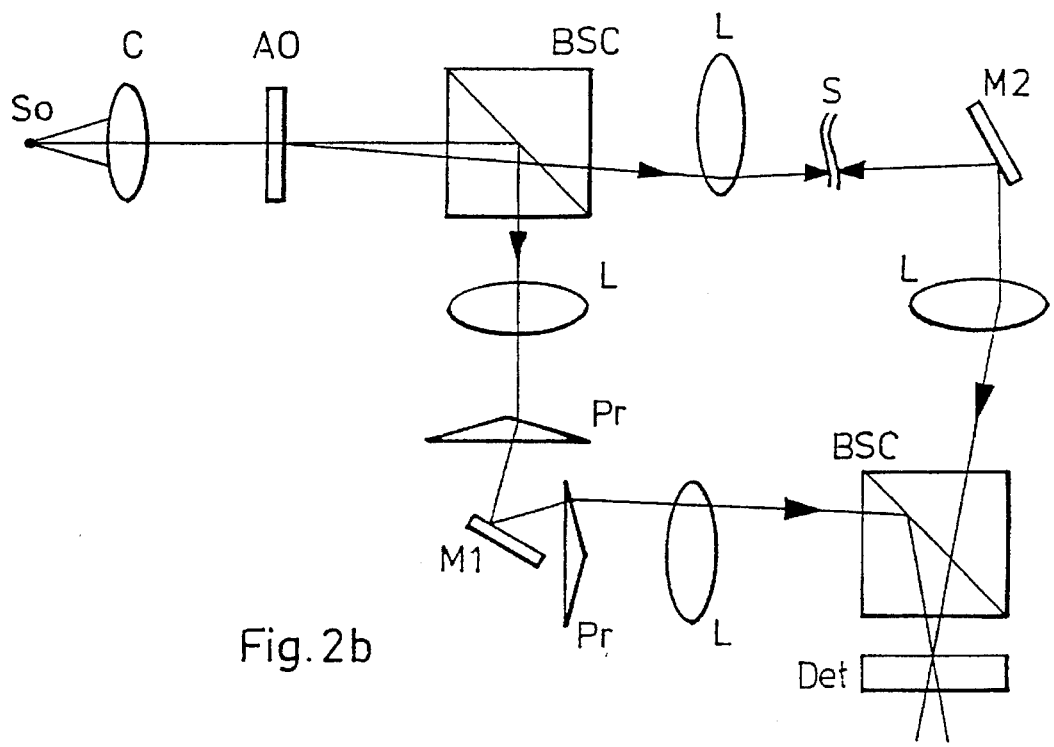
FIG. 2b shows a schematic functional diagram of an inventive transmission configuration for 2D-imaging.

A particularly preferred embodiment of a transmission configuration (relative to the object) is shown in FIG. 2b for 2D-imaging. This is a version of FIG. 2a "folded out" by means of mirrors M1 and M2, e.g. the beams no longer go through the same components. Since the principal of operation corresponds exactly to that of FIG. 2a, a detailed description will not be given here.

Figure 2C:
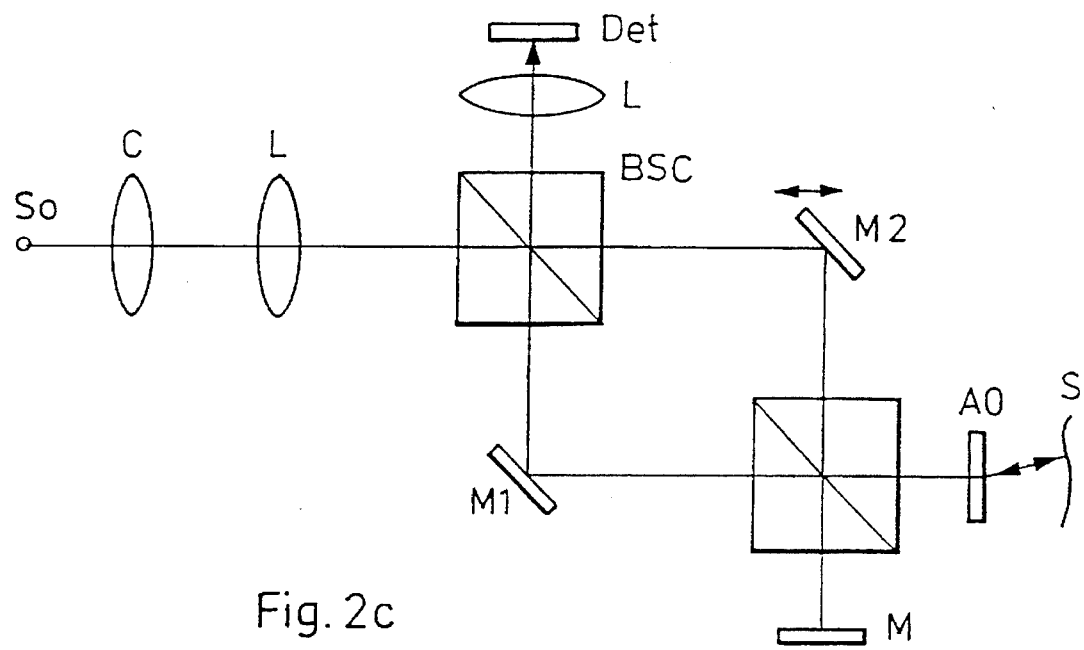
FIG. 2c shows a scheme similar to FIG. 1, whereby a non-mechanical deflection device is integrated into the object arm.

FIG. 2c shows another possible embodiment of a reflection configuration for 2D-imaging which corresponds largely to that of FIG. 1 as was described in detail above. The essential difference with respect to the configuration of FIG. 1 is that a non-mechanical deflection device (for example an acoustical optical modulator AO) is installed in the object arm.

Figure 3:
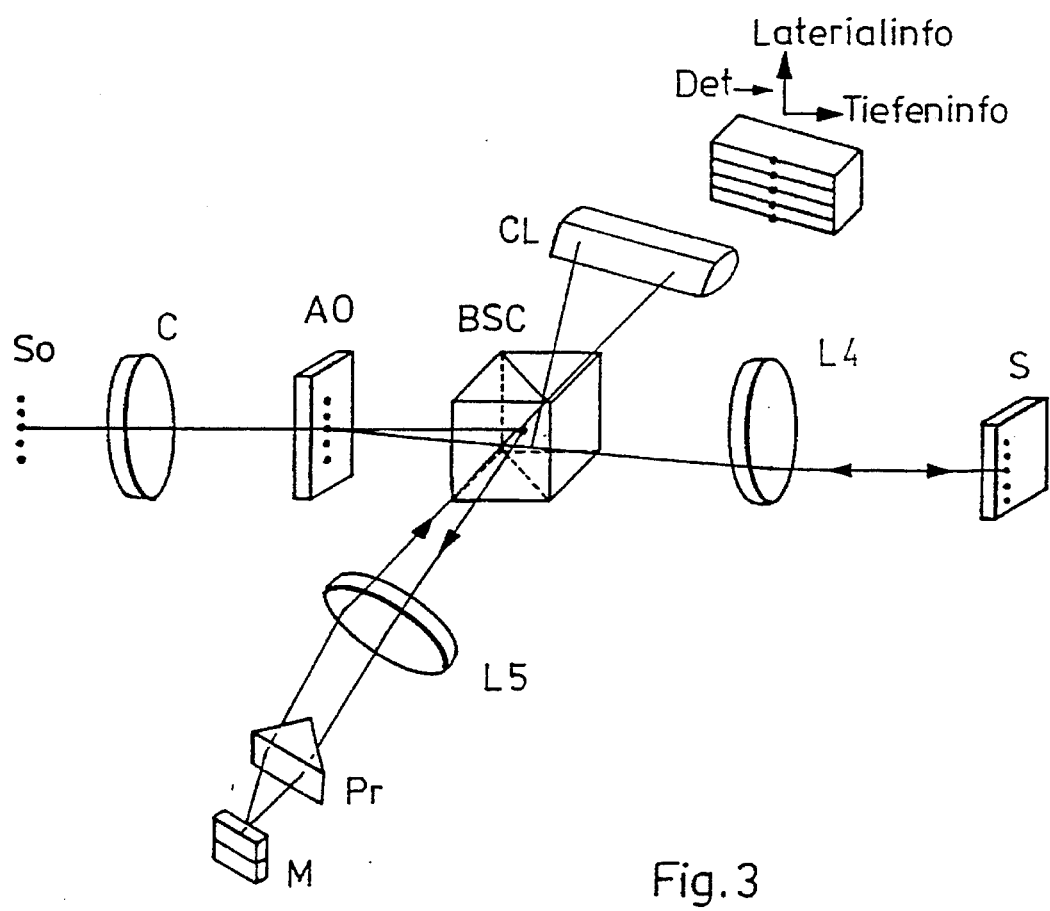
FIG. 3 shows a spatial functional scheme of an inventive reflection configuration for 3D-imaging.

A particularly preferred embodiment of a reflection configuration (relative to the object) is shown in FIG. 3 for 3D-imaging. In this case, the assembly is based principally on that of FIG. 2a. The light source consists, for example, of a 1D-array of point sources So, which produce 1D virtual sources in object S and on the mirror M. A cylindrical lens CL focuses the lateral object information onto an axis of the 2D-detector (for example a CCD-camera), whereas the depth information is transformed onto the other axis. In this fashion, a 2D-image analogous to that of ultrasound is possible in a single "shot". An additional lateral scanning is than possible with the non-mechanical deflection unit (for example AO) for 3D-imaging. Analogous to FIG. 2b a transmission configuration can also be carried out here (not shown).

For 1D- or 2d-imaging limitations one can do without the non-mechanical deflecting device (for example AO). In this case the AC signal which is necessary for the utilization of the lock-in-technique for noise suppression can be produced at the detector by means of a vibrating (instead of the formerly used static) reference mirror.

In the event that an acoustical optical modulator AO is utilized, its intrinsic frequency displacement can be used for producing an AC signal. If the frequency displacement of approximately 80 MHz is too large for the detector utilized it is possible to reduce the AC frequency using the following procedure:

A second AO can, preferentially, be arranged in proximity to the detector exhibiting a slightly different frequency displacement with respect to that of the first AO, whereby only the low frequency difference frequency $\Delta f$ between the two frequencies of the AOs must be processed by the detector.

Through the utilization of a microchannel plate (MCP) in front of the detector and appropriate gate AM-modulation of the MCP it is possible to transform the upwardly modulated frequency shift of AO down to several KHz and below.

The same can be achieved by appropriate AM-modulation of the light source.

The lenses L1–L5, L can, preferentially, exhibit the same focal length which, however, is not absolutely necessary. Areally extended light sources which are relatively inexpensive (simple lamps) can also be used as radiation sources for the inventive configuration. The utilization of fiber optics is also possible with the inventive apparatus, whereby in this event, when bringing the beam reflected from the object and the partial beam from the reference arm of the configuration together onto the detector surface, only small relative angles between both partial beams can be allowed to occur.

The interferometer portion of the inventive configuration is not confined to a stationary Michelson construction, rather a Mach-Zehnder construction, a triangle-interferometer construction, a double mirror-interferometer construction with extended source or a modified Mach-Zehnder interferometer construction with uncollimated light can also be utilized as described in Junttila et al., *J. Opt. Soc. Am. A*, Vol. 8, No. 9 (1991) 1457–1462.

The inventive configuration can also be utilized in spectroscopy or spectro metry, e.g. for the image-like detection of optical parameters such as absorption, transient absorption changes due to non-linear optics effects, scattering coefficients, scattering anisotropies, polarization (M. R. Hee et al., *J. Opt. SOC. AM. B*, Vol. 9, No. 6 (1992) 903–908) or electrical, magnetic or magnetically induced optical effects. By way of example, in absorption measurements (Junttila et al., *J. Opt. Soc. Am. A*, Vol. 8, No. 9 (1991) 1457–1462) the known method for stationary Fourier transformation spectrometry can be incorporated into the imaging method. Spectroscopic information can, in particular with AC-modulation of the relative phases of the partial beams of the inventive configuration, be extracted from the measured carrier frequency, whereby the envelope of the recorded interferogram contains the spatial or structural information concerning the measured object.

Figure 4:
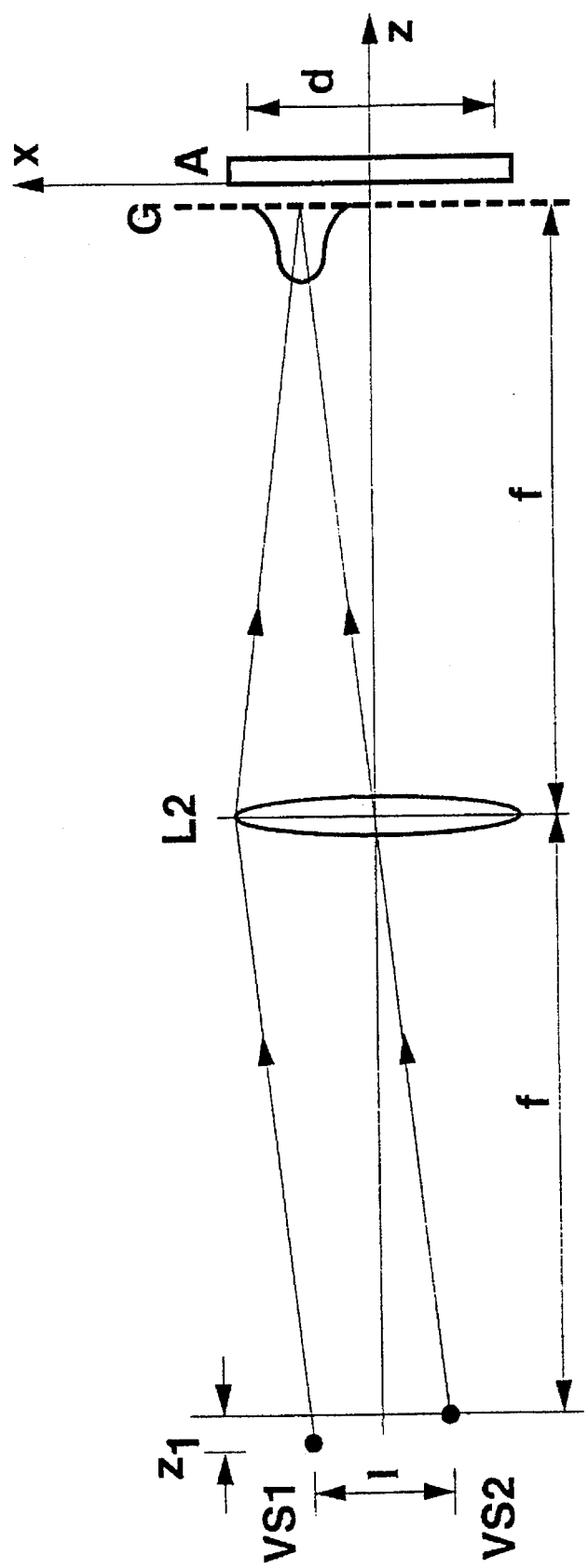
FIG. 4 shows a schematic diagram illustrating the principle of operation of the optical configuration according to FIG. 1.

The fundamental principle for the functioning of the configuration according to FIG. 1 is explained with FIG. 4. In contrast to "classical" interference methods, where the object and reference points lie on the optical axis (are not separated in the lateral direction) herein, both points VS1 and VS2 are laterally separated from another. Beams from object point (VS1) and reference point (VS2) only then interfere with another when both optical path lengths up to a common point on the 1D-detector configuration do not differ from another by more than a coherence length. This can only be achieved for different object depths when the beams exhibit an angle with respect to the optical axis. The signals along the depth direction are transformed temporarily via the angle information into signals along a lateral direction.

FIG. 4 shows an equivalent diagram of the optical system of FIG.1 which is useful for an analysis. VS1 and VS2 are the two virtual sources (with relative coherence) which are arranged at the focal points of sample S and the mirror M3 (see FIG. 1). The separation between the virtual sources is given by $1=21'$, whereby $1'$ represents the relative displacement of the mirror M2 (see FIG. 1). VS2 lies in the forward focal plane of the lens L2. VS1 is a reflection point in the focal point region in the sample and is taken to be displaced by a small separation $z_1$ from the focal plane in the depth direction. The grid G is arranged in the rear focal region of L2 and the detector array A is arranged in close proximity behind G (without the magnifying lens L3 of FIG. 1). A Moire pattern is visible along the diameter d.

It is now possible to derive an expression for the intensity distribution $I(x)$ of the interferogram formed on the detector plane taking into consideration the variables defined in FIG. 4. In the special case of $z_1=0$ the contrast of the interference fringe pattern, due to the optical Fourier transformation construction, does not depend on the extent of the virtual source. Since, in the present case, the difference $z_1$ of the optical path lengths is much less than the focal length of the lens L2, the virtual sources can be treated as point sources. The electric field distribution $E_n(X)$ in the rear focal plane for an object n near the front focal plane is given by $$E_n(X) = K \exp[i(\omega t - k(2f+z_n))] \exp\left[\frac{ikx^2}{2f^2} z_n\right] T_n(U_n) \quad [1]$$

The Fourier transformation $T_n$ $(U_n)$ of the spatial distribution of each (source) object n is a function of the assigned variable $U_n = -x/(\lambda(f+z_n))$, whereby $z_n$ is the optical path difference between the object and the front focal plane in the depth direction. The intensity distribution $I(x)$ of the interferogram (without grid) is given by the square of the sum of the electrical field contributions $E_n(x)$ from both sources. Assuming that the sources exhibit delta function spatial distributions, we obtain $$I(x) = \int S(\upsilon) \left[ 1 + \cos\left( 2\pi\upsilon x - 2\pi\upsilon \frac{f}{l} z_l - 2\pi\upsilon \frac{z_l}{2f} x + 2\pi\upsilon \frac{z_l}{2f} \frac{x^2}{l} \right) \right] d\upsilon \quad [2]$$

whereby $\upsilon = 1/(\lambda_c f)$ is the fundamental spatial frequency corresponding to the average wave length $\lambda_c$ and $S(\upsilon)$ is the spatial intensity distribution of the source. One should notice that we have not taken into consideration the modulation transfer function of the optical set-up in this analysis. Assuming that $S(\upsilon)$ is symmetric, the intensity interferogram $I(x)$ has its maximum when the argument of the cosine function in equation [2] is zero. Independent of the last two (very small) terms in the argument, the optical path transfer function can be defined as $$Tr = \frac{z_l}{x_m} = \frac{l}{f}, \quad [3]$$

whereby the separation $x_m$ from the optical axis lies at the maximum of the intensity interferogram $I(x)$.

The third term of the (cosine) argument of equation [2] shows that the fundamental spatial frequency is displaced by a small guantity $z_1/(2f)$. This is due to the fact that one of the sources lies slightly outside of the focal plane of L2. The fourth term imposes a small linear displacement on the fundamental spatial frequency as a function of x and is even smaller than the third term assuming that $x/l<1$. Since both terms are in the vicinity of $10^{-3}$ or less, they can be neglected.

In the experiment shown here we choose to utilize a grid with a spatial frequency of 80 L/mm in order to convert the intensity interferogram downwards from its fundamental spatial frequency $\upsilon = 1/(\lambda_c f)$. A Moire pattern free of oscillating envelopes is produced in the detector plane in that the separation l (equal to half the displacement of the mirror $M_2$ in FIG. 1) is shifted. With an average wave length of SLD (840 nm) this separation must be 10.08 mm. In accordance with equation [3] this gives an optical path transfer function of Tr=67.2 μm/mm. The upwardly converted spatial frequency does not contribute to the signal because the array executes a low pass filter function since its image element's size is large compared to the grid spacing.

The spatial resolution of the reflectometer is determined by the coherence length of the light source and the resolution of the detector configuration. In order to demonstrate the operation of the reflectometer, the Moire profile of the super-luminescent diode with a linear detector array having low resolution and with a mechanically sampled individual element detector is illustrated. In these experiments the sample is replaced by a mirror. The single element detector is utilized to obtain a profile with high resolution in order to precisely determine the coherence length of the source. The super-luminescent diode (model L3302, Hamamatsu Corp.) emits light with an average wave length of $\lambda_c$=840 nm with a spectral full width at half maximum of $\Delta\lambda$=10 nm for operation with a particular current of 100 mA (1.9 mW power output). Assuming a gaussian spectral form, the source has a theoretical half maximum coherence length of 31 μm at 0.44 $\lambda_c^2/\lambda\Delta$.

Figure 5A:
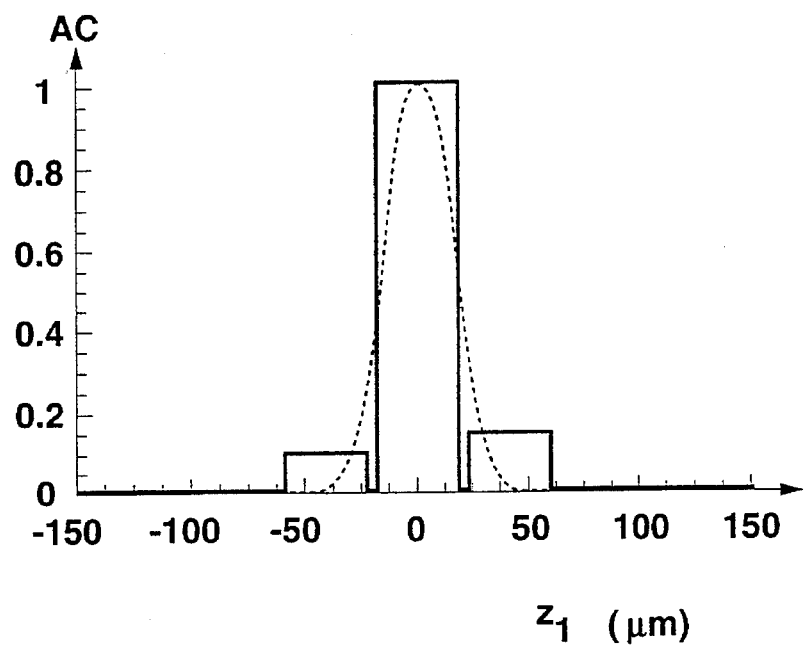
FIG. 5a shows an AC-measured quantity versus the optical path difference $z_1$ (Moire-profile) recorded with a low resolution linear photodiode array (solid line) and a scanned single element photodiode (dashed line)

The interferogram shown in FIG. 5a was taken without a magnifying lens L3. The measured half maximum coherence length (dashed line) was 35 μm. This value is slightly larger than the theoretical value since the diode was operated with a current which was higher than that given (110 mA instead of 100 mA) as a result of which its spectral bandwidth was reduced.

The Moire pattern projected onto the detector configuration does not exhibit any oscillations when the position of M2 is exactly adjusted. The linear 50 element photodiode array (model LD50-5, Centronic, Inc.) of low resolution which was utilized in these experiments consisted of 600 μm wide elements having a separation between the centers of the elements of 700 μm. Without additional enlargement the smallest detectable difference in optical path using the configuration was therefore Tr×700 μm=47 μm (with an optical path transfer function Tr=67.2 μm/mm). This separation is slightly larger than the coherence length as shown in FIG. 5a.

A perfect adjustment of the spatial frequency is important in order to prevent signal loss due to spatial low pass filtering at each image element. The maximum dynamic range of this configuration was ≈−70 dB per image element, which was measured by a spectral analysis apparatus with a one second measuring time.

The maximum optical path length to be detected $z_{lmax}$= Tr×d was approximately 300 μm at a measured width d of the Moire profile of circa 4.5 mm. Although in the ideal case in our apparatus (without magnification) the Moire profile should be visible over the entire diameter (7 mm) of the collimated source beam, the effective width d was smaller since the visibility fell-off towards the direction of the edges of the beam.

In order to increase the spatial resolution achievable with an existing array having low resolution, the edges formed in the plane of the grid are enlarged and projected onto the final image plane. An enlargement factor of circa two resulted in an increase in spatial resolution of 23 μm. Since the array was very long, the maximum optical path difference $z_{lmax}$ was not reduced by the magnification.

Figure 5B:
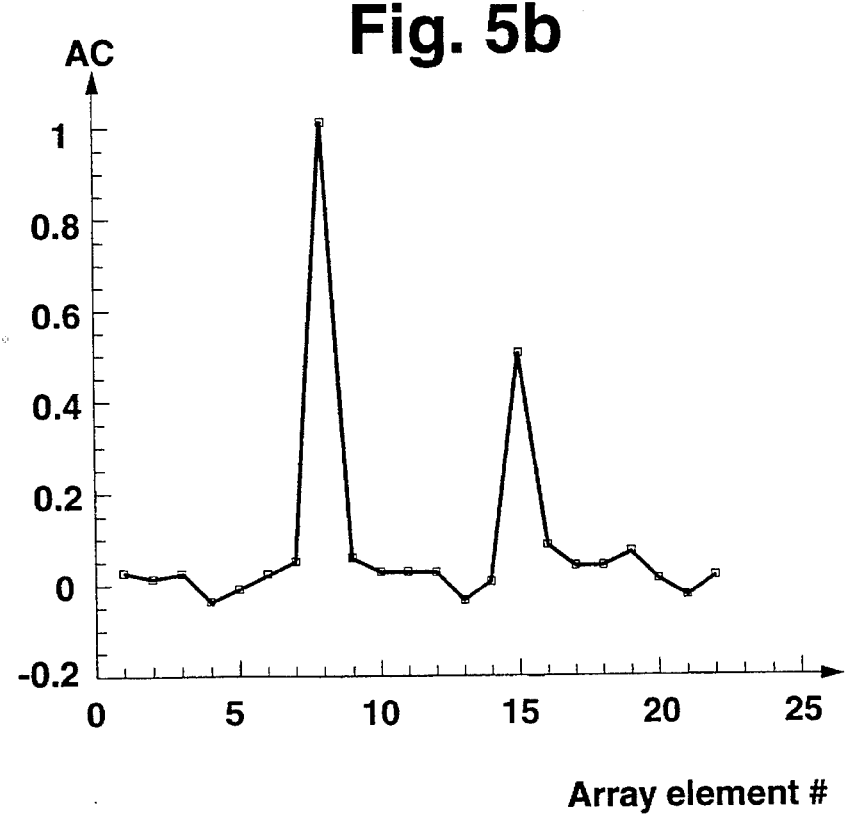
FIG. 5b shows a measured AC-signal versus the array element number from a theoretical measurement application for the determination of the thickness of a plastic film.

As an application, for the purposes of demonstrating the principle, the thickness of a transparent plastic film suspended in air was measured. FIG. 5b shows the forward and rear reflexions of the film. The separation between the two array elements with which the peak reflections occurred corresponded to an optical path difference of 161 μm. Assuming that the film had an index of refraction of 1.4, the actual thickness of this plastic foil was circa 58 μm taking into consideration the doubled path through the sample in the reflection mode. The forward and rear reflections occurred at the imaging elements number 8 and number 15.

The embodiment described in accordance with the inventive configuration, which consists principally of a Michelson interferometer incorporated into a Sagnac type interferometer, can measure a maximum optical path difference of 300 μm (150 μm in depth in the reflection mode) with a resolution of 23 μm (with an additional magnification lens).

Due to spatial overlap from a grid, the coherence length of the source determines the size of the detector element which is necessary to initiate reflections in the sample and not the separation of the edges in the unconverted interferogram.

I claim:

1. An optical imaging apparatus for the investigation of strongly scattering media, having one-dimensional position resolution in a depth direction of a measured object comprising:

a radiation source adapted for the emission of light having a direction and a short coherence length of less than 0.1 mm;

a beam-splitter adapted for splitting the short coherence length light from the radiation source into a first partial beam which is guided in an object arm of the apparatus to be incident on the measured object and a second partial beam which is guided in a reference arm of the apparatus to a reflecting element, the reflecting element being adapted to vibrate with an amplitude of a fraction of a wavelength;

a detector configuration adapted to detect both the second partial beam after reflection from the reflecting element and the first partial beam after reflection from the measured object, the detector configuration having a lateral surface extending transverse to a direction of incidence of the first and the second partial beams which is adapted to record light signals from the two partial beams in a position sensitive and simultaneous fashion; and optical guiding means for transforming the depth direction of the measured object into a lateral displacement along the lateral surface of the beam from detector by directing the first partial beam from the object arm and the second partial beam from the reference arm into a spatial interference pattern at lateral displacements along the lateral surface of the detector configuration response to laterally spaced virtual light sources from the radiation.

2. The optical apparatus of claim 1, wherein the object arm and the reference arm are parts of a Michelson interferometer.

3. The optical apparatus of claim 1, wherein the detector configuration is adapted to record two-dimensional images.

4. The optical apparatus of claim 3, wherein the radiation source includes an array of point-like sources arranged laterally to a direction of the radiation.

5. The optical apparatus of claim 3, further comprising a first device, located along the direction of the radiated light downstream of the radiation source, adapted to non-mechanically laterally deflect the radiated light.

6. The optical apparatus of claim 4, further comprising devices adapted for three-dimensional imaging.

7. The optical apparatus of claim 6, wherein the devices for three-dimensional imaging include a device, arranged along the direction of the radiated light downstream of the radiation source, adapted for non-mechanical lateral deflection of the radiated light.

8. The optical apparatus of claim 5, further comprising a second device for non-mechanical lateral deflection of the radiated light adapted to deflect the light emitted from the source in a direction transverse to a deflection direction of the first deflection device.

9. The optical apparatus of claim 1, further comprising a device adapted for modulation of at least one of a frequency and an amplitude of the light in both partial beams.

10. The optical device of claim 9, wherein the reflecting element is a reflector adapted to vibrate at a defined frequency.

11. The optical apparatus of claim 9, further comprising a non-mechanical deflection device, located in an optical path of the beam-splitter in at least one of the reference arm and the object arm, which is adapted to superimpose a predetermined frequency shift on at least one of the first and the second partial beam.

12. The optical apparatus of claim 9, wherein the modulation device comprises a piezoelectric element.

13. The optical apparatus of claim 11, wherein the deflection device is an acoustic optical modulator.

14. The optical apparatus of claim 11, further comprising a microchannelplate (MCP) located along the direction of the incident light in front of the detector configuration, the MCP having a device for gate controlled amplitude modulation.

15. The optical apparatus of claim 9, further comprising an additional non-mechanical deflection device, located along the direction of the incident light before the detector configuration, adapted to shift back the optical frequency of the light.

16. The optical apparatus of claim 9, wherein the radiation source exhibits a device for amplitude modulation of the emitted light.

17. The optical apparatus of claim 1, wherein the detector configuration comprises a laterally extended photodiode array.

18. The optical apparatus of claim 1, wherein the detector configuration includes a CCD-camera (charge-coupled device).

19. The optical apparatus of claim 1, wherein the radiation source comprises a light emitting diode (LED).

20. The optical apparatus of claim 1, wherein the radiation source comprises a super-luminescent diode (SLD).

21. The optical apparatus of claim 1, wherein the radiation source comprises a short-time or pulsed laser.

22. The optical apparatus of claim 1, wherein the radiation source is laterally extended.

23. The optical apparatus of claim 1, wherein the apparatus is a free space device.

24. An optical imaging apparatus for the investigation of strongly scattering media, having one-dimensional position resolution in a depth direction of a measured object comprising:

a radiation source adapted for the emission of light having a direction and a short coherence length of less than 0.1 mm;

a beam-splitter adapted for splitting the short coherence length light from the radiation source into a first partial beam which is guided in an object arm of the apparatus to be incident on the measured object and a second partial beam which is guided in a reference arm of the apparatus to a reflecting element, the reflecting element being adapted to vibrate with an amplitude of a fraction of a wavelength;

a detector configuration adapted to detect both the second partial beam after reflection from the reflecting element and the first partial beam after reflection from the measured object, the detector configuration having a lateral surface extending transverse to a direction of incidence of the first and the second partial beams which is adapted to record light signals from the two partial beams in a position sensitive and simultaneous fashion; and optical guiding means having an object and an image, the object comprising a first object source formed by the first partial beam and a second object source formed by the second partial beam, the first and the second object sources being laterally separated from another and mutually coherent, the image comprising a spatial interference pattern along the lateral surface of the detector configuration, whereby the depth direction of the measured object is transformed into a lateral displacement along the lateral surface of the detector.

* * * * *